(12) United States Patent  
Loshakove et al.

(10) Patent No.: US 6,726,704 B1
(45) Date of Patent: Apr. 27, 2004

(54) ADVANCED CLOSURE DEVICE

(75) Inventors: Amir Loshakove, Moshav-Bazra (IL); Ido Kilemnik, Herzelia (IL); Dvir Keren, Petach-Tikva (IL)

(73) Assignee: By-Pass, Inc., Orangeburg, NY (US)

( * ) Notice: Subject to any disclaimer, the term of this patent is extended or adjusted under 35 U.S.C. 154(b) by 0 days.

(21) Appl. No.: 09/936,796

(22) PCT Filed: Mar. 20, 2000

(86) PCT No.: PCT/IB00/00302

§ 371 (c)(1),
(2), (4) Date: Sep. 17, 2001

(87) PCT Pub. No.: WO00/56227

PCT Pub. Date: Sep. 28, 2000

Related U.S. Application Data

(63) Continuation-in-part of application No. 09/701,531, filed as application No. PCT/IL99/00284 on May 30, 1999, and a continuation-in-part of application No. 09/701,523, filed as application No. PCT/IL99/00285 on May 30, 1999.

(30) Foreign Application Priority Data

May 29, 1998 (IL) ................................................ 124694
Mar. 19, 1999 (IL) ................................................ 129067

(51) Int. Cl.[7] ............................................. A61B 17/04
(52) U.S. Cl. ...................................................... 606/213
(58) Field of Search ................................ 606/213, 153, 606/155

(56) References Cited

U.S. PATENT DOCUMENTS

| 1,867,624 A | 7/1932 | Hoffman |
| 2,505,358 A | 4/1950 | Gusberg et al. |
| 2,994,321 A | 8/1961 | Tischler |
| 3,104,666 A | 9/1963 | Hale et al. |
| 3,180,337 A | 4/1965 | Smialowski |

(List continued on next page.)

FOREIGN PATENT DOCUMENTS

| DE | 28 22 603 | 11/1979 |
| DE | 31 47 609 | 6/1983 |
| EP | 0 539 237 | 4/1993 |
| EP | 0 916 314 | 5/1999 |
| EP | 1 055 401 | 11/2000 |
| GB | 2 094 212 | 9/1982 |
| IT | 1215699 | 2/1990 |
| WO | WO 89/06515 | 7/1989 |
| WO | WO 89/08433 | 9/1989 |
| WO | WO 96/25886 | 8/1996 |

(List continued on next page.)

OTHER PUBLICATIONS

Copy of Certified Copy of USSN 09/324,997, published on Sep. 14, 2000, Grudem, J. et al., "Medical Grafting Methods and Apparatus".

(List continued on next page.)

*Primary Examiner*—Gary Jackson
(74) *Attorney, Agent, or Firm*—Feaster & Company

(57) ABSTRACT

This invention is a hole closure device (100) having at least two blood vessel engaging structures (106), preferably spikes, each comprising a base (102), at least one second, deformable structure (112) coupled to said at least two blood vessel engaging structures (106), having a first deformation state, and a second deformation state; wherein said at least one second deformable structures (106) urges said two blood vessel engaging structures (106) towards each other when going from said deformation state to said second deformation state; wherein said change in deformation state is at least partially mechanically decoupled from each of said blood vessel engaging structures (106).

33 Claims, 7 Drawing Sheets

U.S. PATENT DOCUMENTS

| | | |
|---|---|---|
| 3,221,746 A | 12/1965 | Noble |
| 3,519,187 A | 7/1970 | Kapitanov et al. |
| 3,586,002 A | 6/1971 | Wood |
| 3,657,744 A | 4/1972 | Ersek |
| 3,776,237 A | 12/1973 | Hill et al. |
| 3,825,010 A | 7/1974 | McDonald |
| 3,837,345 A | 9/1974 | Matar |
| 3,908,662 A | 9/1975 | Razgulov et al. |
| 4,018,228 A | 4/1977 | Goosen |
| 4,069,826 A | 1/1978 | Sessions et al. |
| 4,214,586 A | 7/1980 | Mericle |
| 4,214,587 A | 7/1980 | Sakura, Jr. |
| 4,216,776 A | 8/1980 | Downie et al. |
| 4,352,358 A | 10/1982 | Angelchik |
| 4,366,819 A | 1/1983 | Kaster |
| 4,368,734 A | 1/1983 | Banko |
| 4,368,736 A | 1/1983 | Kaster |
| 4,387,879 A | 6/1983 | Tauschinski |
| 4,485,816 A | 12/1984 | Krumme |
| 4,523,592 A | 6/1985 | Daniel |
| 4,657,019 A | 4/1987 | Walsh et al. |
| 4,676,245 A | 6/1987 | Fukuda |
| 4,696,300 A | 9/1987 | Anderson |
| 4,696,308 A | 9/1987 | Meller et al. |
| 4,846,174 A | 7/1989 | Willard et al. |
| 4,872,874 A | 10/1989 | Taheri |
| 4,917,087 A | 4/1990 | Walsh et al. |
| 4,926,858 A | 5/1990 | Gifford, III et al. |
| 4,930,502 A | 6/1990 | Chen |
| 4,930,674 A | 6/1990 | Barak |
| 4,997,439 A | 3/1991 | Chen |
| 5,009,643 A | 4/1991 | Reich et al. |
| 5,035,702 A | 7/1991 | Taheri |
| 5,041,082 A | 8/1991 | Shiber |
| 5,047,047 A | 9/1991 | Yoon |
| 5,129,913 A | 7/1992 | Ruppert |
| 5,158,566 A | 10/1992 | Pianetti |
| 5,188,636 A | 2/1993 | Fedotov |
| 5,192,294 A | 3/1993 | Blake, III |
| 5,201,901 A | 4/1993 | Harada et al. |
| 5,222,974 A | 6/1993 | Kensey et al. |
| 5,234,447 A | 8/1993 | Kaster et al. |
| 5,234,448 A | 8/1993 | Wholey et al. |
| 5,250,058 A | 10/1993 | Miller et al. |
| 5,254,127 A | 10/1993 | Wholey et al. |
| 5,275,622 A | 1/1994 | Lazarus et al. |
| 5,282,827 A | 2/1994 | Kensey et al. |
| 5,366,462 A | 11/1994 | Kaster et al. |
| 5,392,979 A | 2/1995 | Green et al. |
| 5,403,333 A | 4/1995 | Kaster et al. |
| 5,403,338 A | 4/1995 | Milo |
| 5,425,739 A | 6/1995 | Jessen |
| 5,441,517 A | 8/1995 | Kensey et al. |
| 5,445,632 A | 8/1995 | Blake et al. |
| 5,456,712 A | 10/1995 | Maginot |
| 5,478,353 A | 12/1995 | Yoon |
| 5,478,354 A | 12/1995 | Tovey et al. |
| 5,486,187 A | 1/1996 | Schenck |
| D372,310 S | 7/1996 | Hartnett |
| 5,536,251 A | 7/1996 | Evard et al. |
| 5,540,715 A | 7/1996 | Katsaros et al. |
| 5,562,690 A | 10/1996 | Green et al. |
| 5,562,728 A | 10/1996 | Lazarus et al. |
| 5,618,311 A | 4/1997 | Gryskiewicz |
| 5,658,282 A | 8/1997 | Daw et al. |
| 5,676,670 A | 10/1997 | Kim |
| 5,676,689 A | 10/1997 | Kensey et al. |
| 5,676,696 A | 10/1997 | Marcade |
| 5,690,656 A | 11/1997 | Cope et al. |
| 5,690,662 A | 11/1997 | Chiu et al. |
| 5,695,504 A | 12/1997 | Gifford, III et al. |
| 5,702,412 A | 12/1997 | Popov et al. |
| 5,707,380 A | 1/1998 | Hinchliffe et al. |
| 5,707,393 A | 1/1998 | Kensey et al. |
| 5,709,335 A | 1/1998 | Heck |
| 5,733,308 A | 3/1998 | Daugherty et al. |
| 5,746,755 A | 5/1998 | Wood et al. |
| 5,755,778 A | 5/1998 | Kleshinski |
| 5,758,663 A | 6/1998 | Wilk et al. |
| 5,759,194 A | 6/1998 | Hammerslag |
| 5,779,719 A | 7/1998 | Klein et al. |
| 5,792,173 A | 8/1998 | Breen et al. |
| 5,797,920 A | 8/1998 | Kim |
| 5,797,933 A | 8/1998 | Snow et al. |
| 5,797,934 A | 8/1998 | Rygaard |
| 5,814,005 A | 9/1998 | Barra et al. |
| 5,817,113 A | 10/1998 | Gifford, III et al. |
| 5,823,971 A | 10/1998 | Robinson et al. |
| 5,824,002 A | 10/1998 | Gentelia et al. |
| 5,824,008 A | 10/1998 | Bolduc et al. |
| 5,827,316 A | 10/1998 | Young et al. |
| 5,830,222 A | 11/1998 | Makower |
| 5,833,698 A | 11/1998 | Hinchliffe et al. |
| 5,861,004 A | 1/1999 | Kensey et al. |
| 5,868,763 A | 2/1999 | Spence et al. |
| 5,893,369 A | 4/1999 | LeMole |
| 5,910,153 A | 6/1999 | Mayenberger |
| 5,910,155 A | 6/1999 | Ratcliff et al. |
| 5,922,000 A | 7/1999 | Chodorow |
| 5,931,842 A | 8/1999 | Goldsteen et al. |
| 5,935,147 A | 8/1999 | Kensey et al. |
| 5,948,425 A | 9/1999 | Janzen et al. |
| 5,957,973 A | 9/1999 | Quiachon et al. |
| 5,964,782 A | 10/1999 | Lafontaine et al. |
| 5,972,014 A | 10/1999 | Nevins |
| 5,976,159 A | 11/1999 | Bolduc et al. |
| 5,976,178 A | 11/1999 | Goldsteen |
| 5,993,468 A | 11/1999 | Rygaard |
| 5,993,476 A | 11/1999 | Groiso |
| 6,004,330 A | 12/1999 | Middleman et al. |
| 6,004,341 A | 12/1999 | Zhu et al. |
| 6,022,367 A | 2/2000 | Sherts |
| 6,026,814 A | 2/2000 | LaFontaine et al. |
| 6,035,856 A | 3/2000 | LaFontaine et al. |
| 6,036,702 A | 3/2000 | Bachinski et al. |
| 6,071,292 A | 6/2000 | Makower et al. |
| 6,113,612 A | 9/2000 | Swanson et al. |
| 6,152,937 A | 11/2000 | Peterson et al. |
| 6,165,185 A | 12/2000 | Shennib et al. |
| 6,176,867 B1 | 1/2001 | Wright |
| 6,190,353 B1 | 2/2001 | Makower et al. |
| 6,193,734 B1 | 2/2001 | Bolduc et al. |
| 6,197,042 B1 | 3/2001 | Ginn et al. |
| 6,251,116 B1 | 6/2001 | Shennib et al. |
| 6,383,208 B1 | 5/2002 | Sancoff et al. |
| 6,391,036 B1 | 5/2002 | Berg et al. |
| 6,391,038 B2 | 5/2002 | Vargas et al. |
| 6,398,797 B2 | 6/2002 | Bombard et al. |
| 6,402,764 B1 | 6/2002 | Hendricksen et al. |
| 6,419,681 B1 | 7/2002 | Vargas et al. |
| 6,485,496 B1 | 11/2002 | Suyker et al. |
| 6,588,643 B2 | 7/2003 | Bolduc et al. |
| 2001/0016752 A1 | 8/2001 | Berg et al. |

FOREIGN PATENT DOCUMENTS

| | | |
|---|---|---|
| WO | WO 96/33673 | 10/1996 |
| WO | WO 97/13463 | 4/1997 |
| WO | WO 97/13471 | 4/1997 |
| WO | WO 97/27898 | 8/1997 |
| WO | WO 97/28749 | 8/1997 |
| WO | WO 97/40754 | 11/1997 |

| | | |
|---|---|---|
| WO | WO 98/19629 | 5/1998 |
| WO | WO 98/19634 | 5/1998 |
| WO | WO 98/19635 | 5/1998 |
| WO | WO 98/19636 | 5/1998 |
| WO | WO 98/30152 | 7/1998 |
| WO | WO 98/32412 | 7/1998 |
| WO | WO 98/38922 | 9/1998 |
| WO | WO 98/38939 | 9/1998 |
| WO | WO 98/38941 | 9/1998 |
| WO | WO 98/38942 | 9/1998 |
| WO | WO 98/42262 | 10/1998 |
| WO | WO 98/55027 | 12/1998 |
| WO | WO 98/57591 | 12/1998 |
| WO | WO 98/57592 | 12/1998 |
| WO | WO 99/21491 | 5/1999 |
| WO | WO 99/37218 | 7/1999 |
| WO | WO 99/38441 | 8/1999 |
| WO | WO 99/40851 | 8/1999 |
| WO | WO 99/62415 | 12/1999 |
| WO | WO 99/65409 | 12/1999 |
| WO | WO 00/27311 | 5/2000 |
| WO | WO 00/27312 | 5/2000 |
| WO | WO 00/27313 | 5/2000 |
| WO | WO 00/45886 | 8/2000 |
| WO | WO 00/53104 | 9/2000 |
| WO | WO 00/66007 | 11/2000 |
| WO | WO 00/69343 | 11/2000 |
| WO | WO 00/69346 | 11/2000 |
| WO | WO 00/69349 | 11/2000 |
| WO | WO 00/69364 | 11/2000 |
| WO | WO 00/72764 | 12/2000 |
| WO | WO 00/74579 | 12/2000 |
| WO | WO 01/08566 | 2/2001 |
| WO | WO 01/15607 | 3/2001 |
| WO | WO 01/15609 | 3/2001 |
| WO | WO 01/17440 | 3/2001 |
| WO | WO 01/19256 | 3/2001 |
| WO | WO 01/19259 | 3/2001 |
| WO | WO 01/26562 | 4/2001 |
| WO | WO 01/30444 | 5/2001 |
| WO | WO 02/13702 | 2/2002 |

OTHER PUBLICATIONS

Copy of Certified Copy of USSN 60/137,764, published on Dec. 14, 2000, Logan, J. et al., "Mechanical Anastomosis Delivery Apparatus".

Copy of Ceritifed Copy of USSN 09/187,361, published on May 18, 2000, Galdonik, J. A. et al., "Medical Graft Component and Methods of Installing Same".

Copy of Certified Copy of USSN 09/187,364, published on May 18, 2000, Berg, T. A. et al., "Minimally Invasive Revascularization Apparatus and Methods" 6,475,222.

Draney, M. et al.; "Coronary Artery Bypass Surgery: Minimally Invasive Techniques"; May 1998; Retrieved from Internet: <http://roe210abc.stanford.edu/94–95/projects/Pflizer.Spring/1.htm>.

Obora, Y. et al., "Nonsuture Microvascular Anastomosis Using Magnet Rings: Preliminary Report"; Feb. 1978; pp. 117–120; Sur Neurol (United States); vol. 9, No. 2.

Ostrup, L. T. et al.; "The UNILINK Instrument System for Fast and Safe Microvascular Anastomosis"; pp. 521–526; Department of Plastic Surgery, Hand Surgery, and Burns; University Hospital, Sweden; presented in part at the First Scandinavian Seminar on Reconstructive Microsurgery, Sweden, Oct. 1979, and at the Symposium on MicroneurovascularSurgery, Denmark, Jan. 1983.

Yachia, D. et al.; "Bio–Fragmentable Anastomosis Ring in Urological Surgery Involving the Gastrointestinal Tract: Early Experiences and a Historical Review of Mechanical Intestinal Anastomosis"; May 1995; pp. 1426–1428; The Journal of Urology; vol. 153.

ADVANCED CLOSURE DEVICE

RELATED APPLICATIONS

This application is a national phase filing of PCT/IB00/00302, filed Mar. 20, 2000. This application is a continuation in part of PCT applications PCT/IL99/00284, filed May 30, 1999 now U.S. Ser. No. 09/701,531, filed Nov. 28, 2000 PCT/IL99/00285, filed May 30, 1999 now U.S. Ser. No. 09/701,523, filed Nov. 28, 2000 PCT/IL99/00670 filed Dec. 8, 1999 and PCT/IL99/00674, filed Dec. 9, 1999 the disclosures of which are incorporated herein by reference.

FIELD OF THE INVENTION

The present invention relates to hole closure devices for blood vessels.

BACKGROUND OF THE INVENTION

Many medical procedures require forming holes in blood vessels. After the procedure is completed, the holes must be closed, to prevent a fatal hemorrhage. Typically, such holes are closed using sutures, or by applying pressure against the hole.

U.S. Pat. No. 5,938,425 to Janzen et al., the disclosure of which is incorporated herein by reference, suggests sealing a hole by providing a sealing material outside of the hole.

U.S. Pat. No. 5,964,782 to Lafontaine et al., the disclosure of which is incorporated herein by reference, describes a catheter having hooks at its ends for bringing the sides of a hole together, for sealing by pressure or by electro-coagulation.

SUMMARY OF THE INVENTION

It is an object of some preferred embodiments of the invention to provide an implanted device for sealing holes in a blood vessel, the device having a smaller chance of retraction of spikes, barbs or other tissue engagement elements of the device, from the blood vessel, than devices of the prior art.

An aspect of some preferred embodiments of the invention relates to mechanically decoupling the spikes of a hole closure device from a part of the device that controls the device general geometry. Thus, the deformation of the spikes does not affect the device geometry and vice-versa. In a preferred embodiment of the invention, this results in a separation between the forces that change the device geometry to close the hole and the forces that maintain the spikes in side the blood vessel. This separation is expected to prevent the geometric distortion of the device from inadvertently retracting the spikes form the blood vessel.

In a preferred embodiment of the invention, the decoupling is achieved by assuring that energy stored by the device for closing the hole in the blood vessel is not stored in the spikes or in structures that spring-load the spikes. Thus, release of the energy is less likely to affect the hold of the spikes on the vessels. In plastically deformed devices, the spikes are configured so that the plastic deformation does not affect the spikes or parts of the device that spring-load the spikes.

An aspect of some preferred embodiments of the invention relates to providing a pivot bar for vessel-engaging spikes of a hole closure device. Preferably, the pivot bar is not part of the load bearing structure of the device. A potential advantage of using a pivot bar is that a spike can be rotated around the pivot bar without bending the spike and without and protrusion from the plane of the device and/or the surface of the blood vessel. Preferably, the pivot bar defines at its ends or along its length hinges (or weakened points) for controlling the twisting of the bar relative to the rest of the device, however, this is not necessary.

An aspect of some preferred embodiments of the invention relates to spacing the spike used to engage the blood vessel away from a hole in the blood vessel. Preferably, this results in a lower probability of the spike inadvertently retracting from the blood vessel.

An aspect of some preferred embodiments of the invention relates to a hole-closure device design, in which two concentric structures are provided, an inner structure for controlling the device geometry and an outer structure for supporting spikes and/or other means of engaging the blood vessel. Optionally, the spikes are coupled to the inner structure only through tab means provided to bend the spikes out of plane.

An aspect of some preferred embodiments of the invention relates to providing a hinge in a hole closure device. In a preferred embodiment of the invention, when the device distorts to close a hole, the distortion is controlled by the hinge, for example, being focused at the hinge or being prevented at the hinge. Preferably, the hinge is integral with the device. Alternatively, the device is formed of two or more parts attached to each other by the hinge. In a preferred embodiment of the invention, the device is designed for sealing an elongate cut in a blood vessel, by deforming between a substantially round configuration to a substantially ellipsoid configuration.

In a preferred embodiment of the invention, a multiple part device is provided, with all of the multiple parts being outside of the blood vessel and, preferably, being substantially equivalent in function.

An aspect of some preferred embodiments of the invention relates to a bi-stable hole closure device. In a preferred embodiment of the invention, the device has at least two stable states, a first state in which the device defines an open lumen through which a catheter, cannula or other tube may be provided and a second state in which the lumen is significantly contracted or even closed.

An aspect of some preferred embodiments of the invention relates to an elastic clip for closing a hole in a blood vessel. In a preferred embodiment of the invention, the clip is maintained in an open configuration, suitable for engaging a blood vessel, by inserting a spacer in the clip. After engaging the blood vessel, the spacer is moved or removed, so the clip can close. Preferably, the closure is elastic, super elastic or shape-memory based. Alternatively, the closure may be plastic, as a result of the application of force.

There is thus provided in accordance with a preferred embodiment of the invention, a hole closure device, comprising:

at least two blood vessel engaging structures, each comprising a base;

at least one second, deformable, structure, coupled to said at least two blood-vessel engaging structures and having a first deformation state and a second deformation state, wherein said at least one second deformable structure urges said two blood vessel engaging structures towards each other when going from said first deformation state to said second deformation state, wherein, said change in deformation state is at least partially mechanically decoupled from each of said blood-vessel engaging structures, such that it does not effect a substantial deformation of said blood-vessel engaging structure relative to said base.

Preferably, said at least one second deformable structure comprises a deformable ring-like structure, adapted to enclose a blood vessel cannula-like tube in said first deformation state. Preferably, the device comprises a ring-like element on which said at least one deformable structure is mounted and wherein said at least one second deformable structure comprises at least two bending elements that couple said blood-vessel engaging structures to said ring-like element. Preferably, said ring-like element defines a lumen that has a substantially same radius in said deformation states. Alternatively, said blood vessel engaging structures each comprise at least one spike adapted for insertion into a wall of a blood vessel.

In a preferred embodiment of the invention, said blood vessel engaging structures each comprise at least two spikes adapted for insertion into a wall of a blood vessel. Preferably, said blood vessel engaging structures each comprise a pivot bar on which said spike is mounted.

In a preferred embodiment of the invention, said blood vessel engaging structures each comprise at least one tab, mounted on said pivot bar. Preferably, said tab comprises an anchor for holding said tab. Alternatively or additionally, said pivot bar comprises a hinge at either end.

In a preferred embodiment of the invention, said pivot bar is straight. Alternatively or additionally, said pivot bar is mounted on a spacer that spaces said pivot bar from said at least one second deformable structure.

In a preferred embodiment of the invention, said base is adapted for abutment against the blood vessel. Preferably, said bases are spaced apart a distance sufficient to prevent eversion of a blood vessel in which a hole is closed. Alternatively, said bases are spaced apart a distance sufficient to cause at least partial eversion of a blood vessel in which a hole is closed.

In a preferred embodiment of the invention, said at least one second deformable structure comprises at least two deformable structures connected by at least one joint. Preferably, said joint is elastic. Alternatively or additionally, said joint comprises a segment of a circle.

Alternatively, said joint is free turning for at least a range of angles.

In a preferred embodiment of the invention, said joint is integral with said at least two deformable structures.

In a preferred embodiment of the invention, said joint is formed by an interlocking of the two deformable structures.

In a preferred embodiment of the invention, said at least one deformable structure comprises a bar.

In a preferred embodiment of the invention, at least one of said blood vessel engaging structures is radially external to said at least one deformable structure. Alternatively or additionally, at least one of said blood vessel engaging structures is radially internal to said at least one deformable structure.

There is also provided in accordance with a preferred embodiment of the invention, a hole closure device, comprising:
   at least one pivot bar;
   at least one spike mounted on said spike such that rotating said spike around said bar twists said pivot bar; and
   a base to which said at least one bar is coupled and which base does not encompass said bar. Preferably, the device comprises at least one structure which supports said pivot bar and which couples said pivot bar to said base.

Alternatively or additionally, said base comprises a deformable ring-like element. Preferably, said base comprises at least two hinges at opposite ends of said base.

There is also provided in accordance with a preferred embodiment of the invention, a hole closure device, comprising:
   a deformable ring-like structure;
   a plurality of spikes coupled to said structure, each of said spike comprising a base; and
   a coupling structure coupling said base to said ring-like structure, wherein said base is radially spaced from said ring-like structure by said coupling structure, at least the length of said spike. Preferably, said spikes are each mounted on a pivot bar.

There is also provided in accordance with a preferred embodiment of the invention, a hole closure device comprising:
   a first body part comprising:
      a plurality of blood-vessel engaging structures, adapted to remain outside a blood vessel; and
      at least a first hinge part coupled to said plurality of blood vessel engaging structures; and
   a second body part comprising:
      a plurality of blood-vessel engaging structures adapted to remain outside a blood vessel; and
      at least a second hinge part coupled to said plurality of blood vessel engaging structures,
   wherein said first and said second hinge parts are adapted to interlock to form a hinge.

There is also provided in accordance with a preferred embodiment of the invention, a blood vessel clip, comprising:
   at least two spikes;
   at least one tab, perpendicular to at least one of said spikes; and
   an elastic body connecting the two spikes, said body having a greater inner dimension away from said spike than nearer said spike.

There is also provided in accordance with a preferred embodiment of the invention, a bi-stable hole closure device, comprising:
   at least two arms, coupled to each other at either end thereof, wherein:
      a first one of said arms is less flexible than a second one of said arms, and wherein said second arm is adapted to have two stable states, one state in which the second arm is spaced from said first arm and one state in which said second arm is adjacent said first arm; and
   a plurality of blood-vessel engaging elements mounted on each of said arms.

BRIEF DESCRIPTION OF THE DRAWINGS

Particular embodiments of the invention will be described with reference to the following description of preferred embodiments in conjunction with the figures, wherein identical structures, elements or parts which appear in more than one figure are preferably labeled with a same or similar number in all the figures in which they appear, in which.

DETAILED DESCRIPTION OF PREFERRED EMBODIMENTS

Figure 1A:
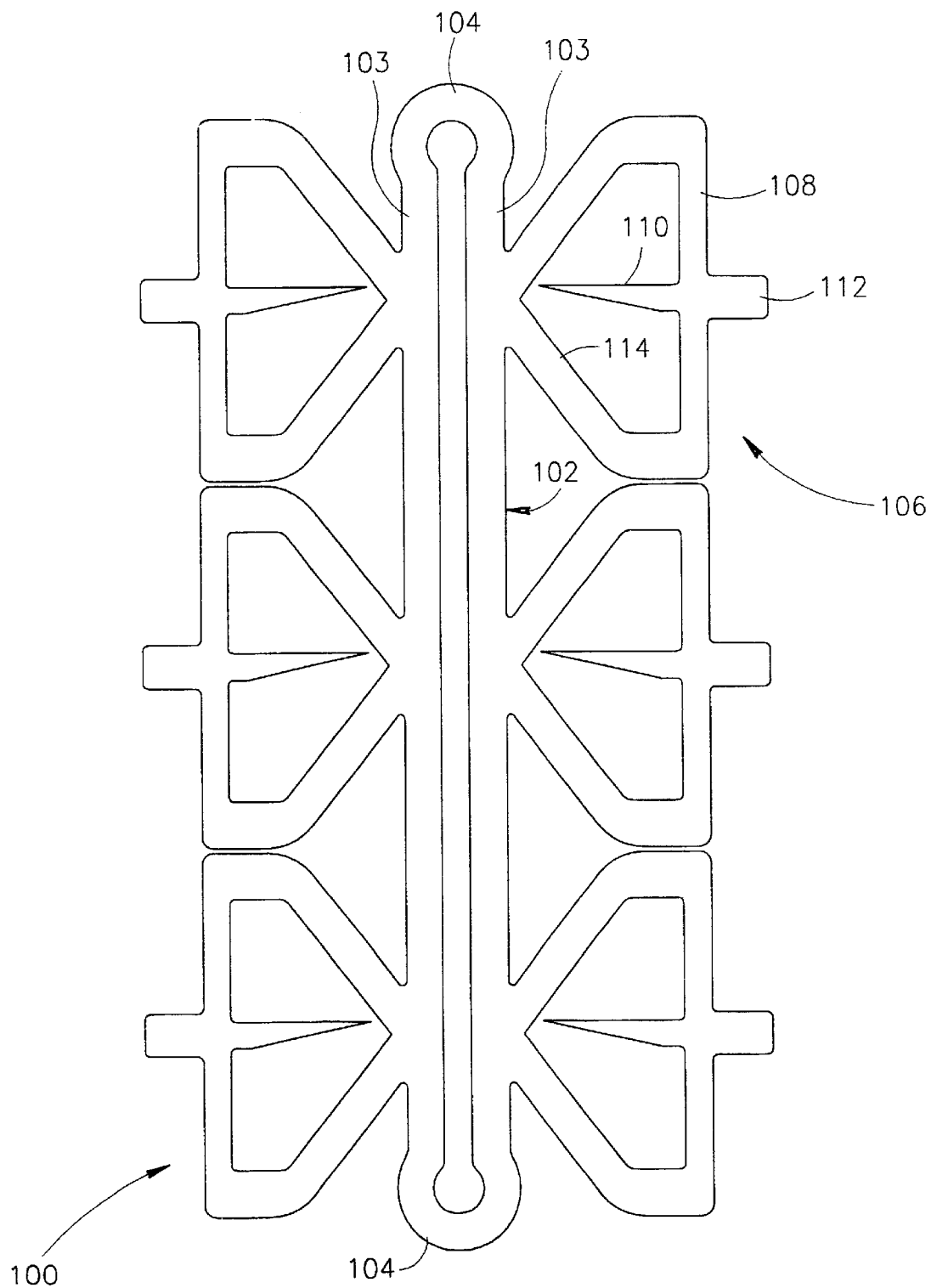
FIG. 1A is a plan view of a hole closure device in accordance with a preferred embodiment of the invention.

FIG. 1A is a plan view of a hole closure device 100, in accordance with a preferred embodiment of the invention. Device 100 comprises a body section 102 and a plurality of spike sections 106 attached to body section 102. Although six such sections are shown, the number may vary depending on the use of the device, for example, being 2, 3, 4, 5, 7, 9 or more. In the exemplary device shown, body section 102 comprises two elongate elements 103, attached together at their ends by hinges 104. The design of hinges 104 is such that when device 100 is distorted for implantation to define a circular or elliptical lumen (See FIGS. 1B–1C), a significant part of the distortion is concentrated at the hinges.

In the exemplary device shown, a spike section 106 comprises a pivot bar 108, having a spike 110 mounted on one side and a tab 112 mounted on another side thereof. A spacing structure 114 spaces bar 108 from body section 102. In an alternative device, the lumen of device 100 is defined by alternating ring segments and spike sections. Alternatively, the spike sections may be inside the ring segment, so they are not spaced away from the lumen of the device.

It should be noted that since tab 112 is coupled to bar 108, it is not required that tab 112 be opposite spike 110 in order to control the positions of the spikes. Further, a plurality of spikes 110 and/or tabs 112 may be provided on each spike section 106. Also, tab(s) 112 and spike(s) 110 do not all have to be in a same plane. Preferably, the tabs are not in a same plane as the spikes, so that when deployment is complete (FIG. 1E, below), the tabs can be flat with the surface of the blood vessel. Thus, the tabs may also be curved.

Although a straight bar is shown, the bar may be curved or angular. Thus, in some embodiments, the bar is radially expandable or can provide elastic force perpendicular to the bar, along the spike.

The spikes may be long or short (relative to the length of pivot bar 108 and the distance of bar 108 from body section 102). Although straight spikes are preferred, curved spikes, curved in either of the two directions perpendicular to the spike, may be used. As shown, bar 108 does not include designated twisting regions. Alternatively one or more such regions, which twist more or less than the rest of bar 108, may be provided. In one example, a more easily twisting region is provided at each of the ends of bar 108. Twisting areas may be, for example, thinner, narrower or include apertures.

Figure 1B:
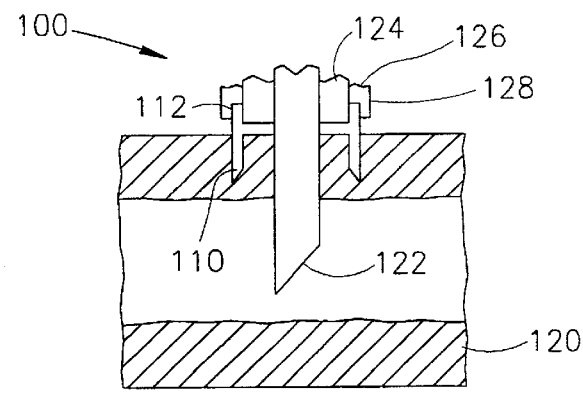
FIGS. 1B–1E illustrate the deployment of the device of FIG. 1, in accordance with a preferred embodiment of the invention.

FIGS. 1B–1E illustrate the deployment of device 100, in accordance with a preferred embodiment of the invention. In FIG. 1B, device 100 is mounted on a cannula 122, that pierces a blood vessel 120. In a preferred embodiment of the invention, tabs 112 are held by a tab holding tube 126 against a contra-element tube 124. Tab-holding tube 126 may include thinner portions 128 for defining a hollow between tube 126 and tube 124, for the tabs. As spikes 110 are preferably pointed axially with the cannula, closure device 100 can be advanced along cannula 122 to engage blood vessel 120, as shown.

Figure 1C:
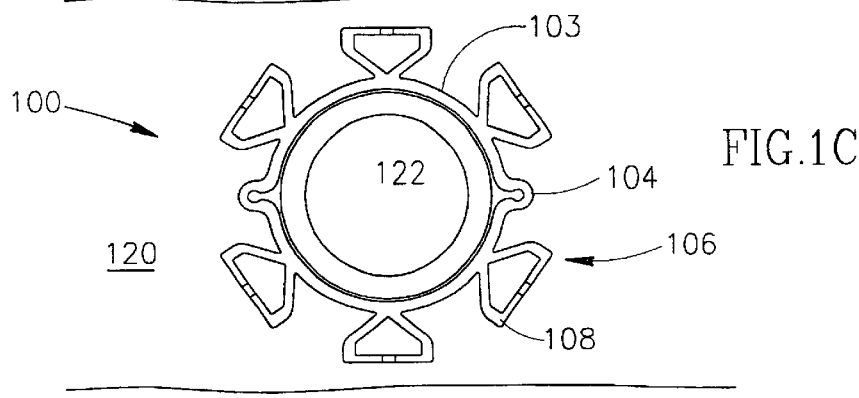

FIG. 1C is a top view along the cannula axis, with the holding and contra tubes 124 and 126 not shown. Body section 102 of device 100 is shown distorted to define a lumen through which cannula 122 is provided.

Figure 1D:
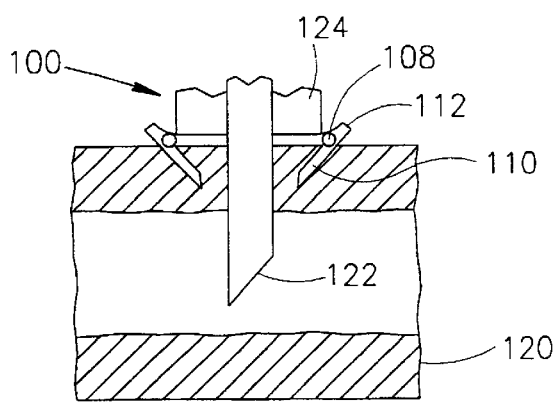

FIG. 1D shows the effect of removing tab holding tube 126, which allows the pivot bar 108 to partially twist back so that spikes 110 engage vessel 120 better.

Figure 1E:
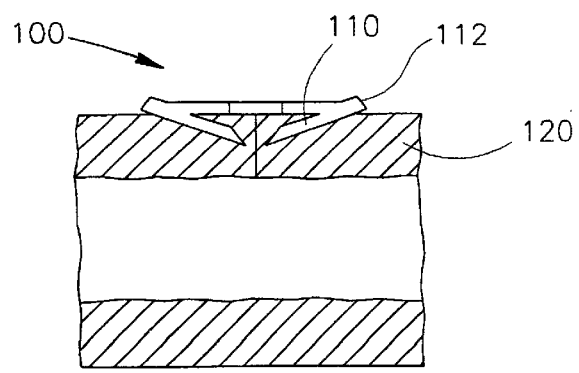

In FIG. 1E, the cannula is removed, allowing body section 102 to revert to its previous geometry. Since spikes 110 are pulled along by body section 102 and engage vessel 120, when body section 102 distorts back, the hole in vessel 120 is closed.

Figure 2A:
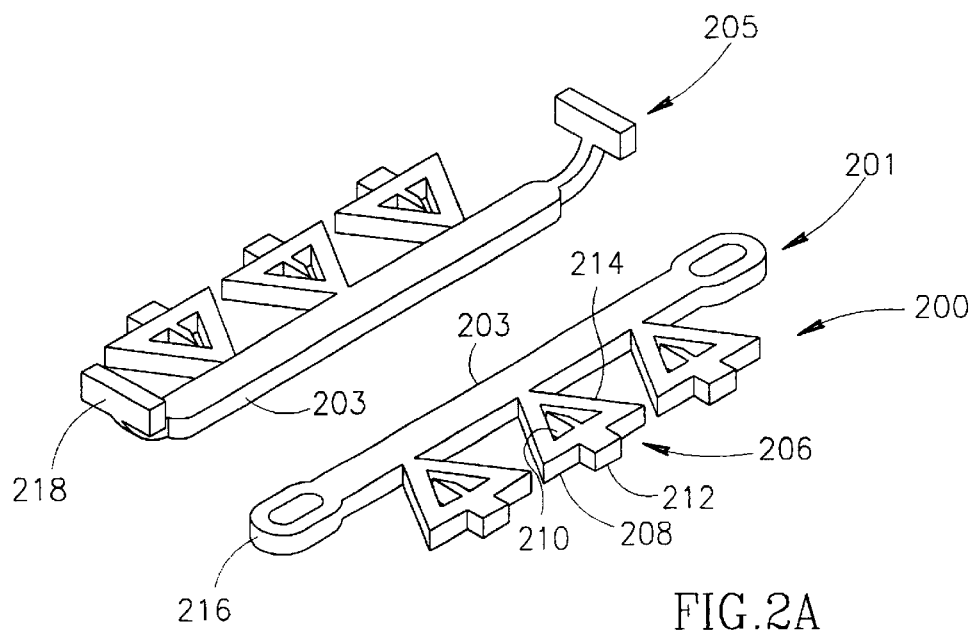
FIG. 2A is a perspective view of a two part hole closure device, in accordance with a preferred embodiment of the invention.

FIG. 2A is a perspective view of a multi-part hole closure device 200, in accordance with a preferred embodiment of the invention. Device 200, as shown, comprises only two parts 201 and 205, however, a larger number of device segments could be provided as well, for example the device being formed of three or four links. Each of parts 201 and 205 comprises an elongate element 203 and a plurality of spike sections 206, corresponding to the same parts in FIG. 1C. Parts 201 and 205 have, at the ends of elements 203, hinge parts, for example an eye 216 on part 201 and a hook 218 on part 205. Hook 218 and eye 216 engage to form a hinge. Other interlocking element types may also be used. Alternative types of joints may be provided, for example crimp joints that are formed by crimping the hinge parts together or by deforming one or both of the hinge parts. It is noted that unlike hinge 104 of device 100, the hinge of device 200 does not necessarily (although it may) store any elastic energy when the device is distorted. Rather, any such energy is preferably stored by bending body elements 203.

Figure 2B:
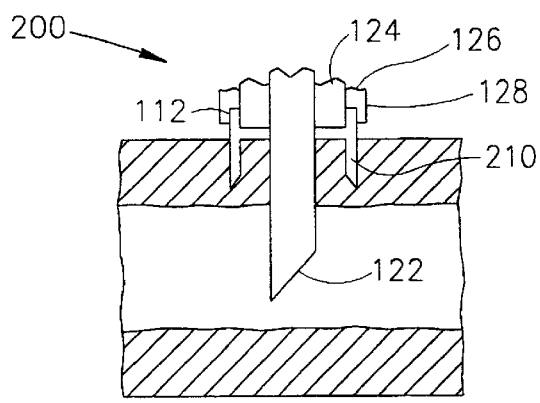
FIGS. 2B and 2C show the device of FIG. 2A, during deployment, in accordance with a preferred embodiment of the invention.

FIG. 2B shows device 200 on a cannula 122. The mounting method can be exactly the same as that of FIG. 1B.

Figure 2C:
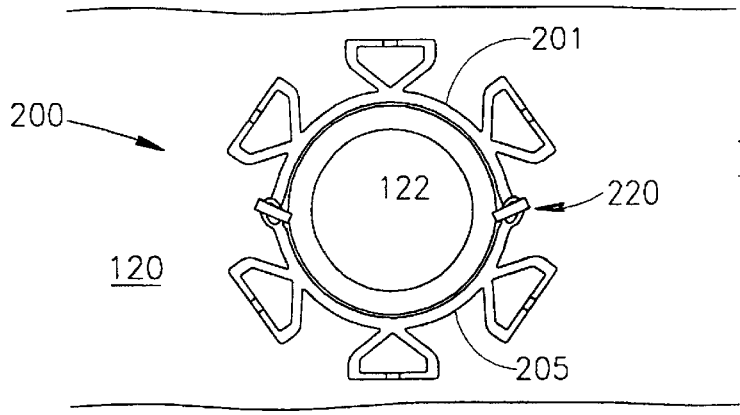

FIG. 2C is a top view along the cannula axis, with the holding and contra tubes 124 and 126 not shown. This figure is also very similar to FIG. 1C, with an important difference, a hinge 220 is provided by the interlocking of eye 216 and hook 218.

Figure 3A:
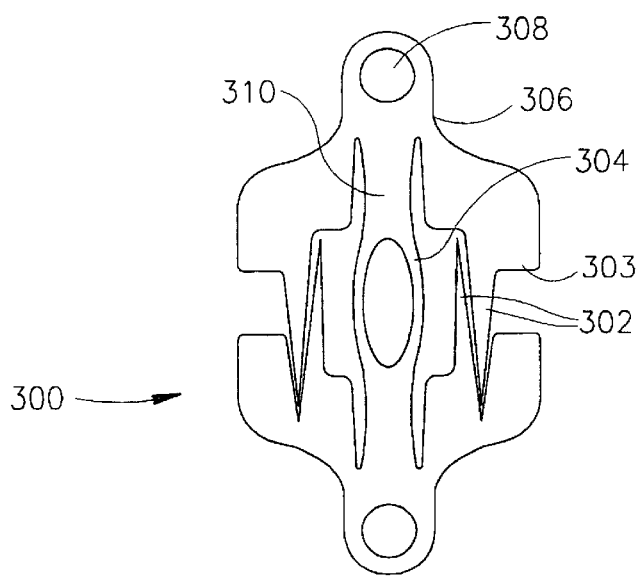
FIGS. 3A–3C illustrate hole closure devices in accordance with preferred embodiments of the invention.
Figure 3B:
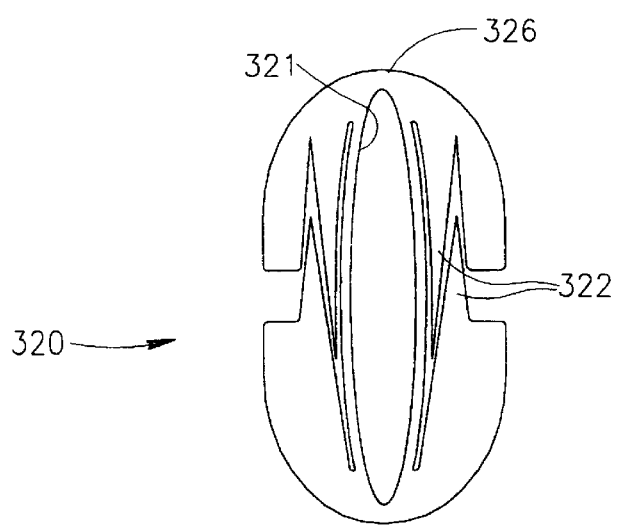
Figure 3C:
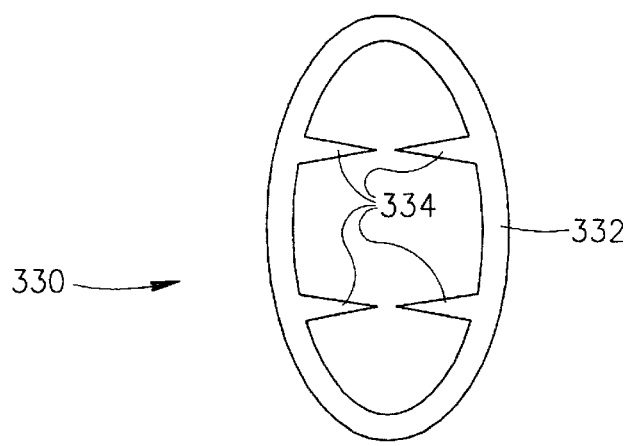

FIGS. 3A–3C illustrate hole closure devices in accordance with preferred embodiments of the invention.

FIG. 3A illustrates a device 300, in which a plurality of spikes 302 are defined to be outside of a structural ring 304 of the device. In some embodiments of the invention, ring 304 does not distort during deployment. A pair of tabs 306 are provided, each tab associated with two of spikes 302, such that when the tabs are bent, the spikes also twist with them. Preferably, a bending strip 310 is provided as a hinge between tab 306 and ring 304. It is noted that spikes 302 are coupled to ring 304 only via tab(s) 306, so that they are substantially decoupled from ring 304. Tab 306 may include an anchor, such as a hole 308, for engagement during deployment. Spikes 302 preferably comprise a base portion 303 that is substantially wider than the spike.

FIG. 3B illustrates a device 320 which is a variant of device 300, in which an inner ring 321 extends to the ends of device 320 and takes over the function of holes 308 and/or bending strip 310. Tabs 326 are significantly shorter than tabs 306.

FIG. 3C illustrates a simpler device 330, in which a plurality of spikes 334 are mounted on a ring 332. As shown, spikes 334 are wide at their base, preventing the spikes themselves from bending, when ring 332 is twisted. A particular feature of this device (and some of the previous devices) is that a lumen remains in the device even after the hole is closed. This lumen is useful if an attempt is made to insert a cannula again into the vessel, at the device location. The cannula would be able to enter through the lumen, without damaging the blood vessel.

Figure 3D:
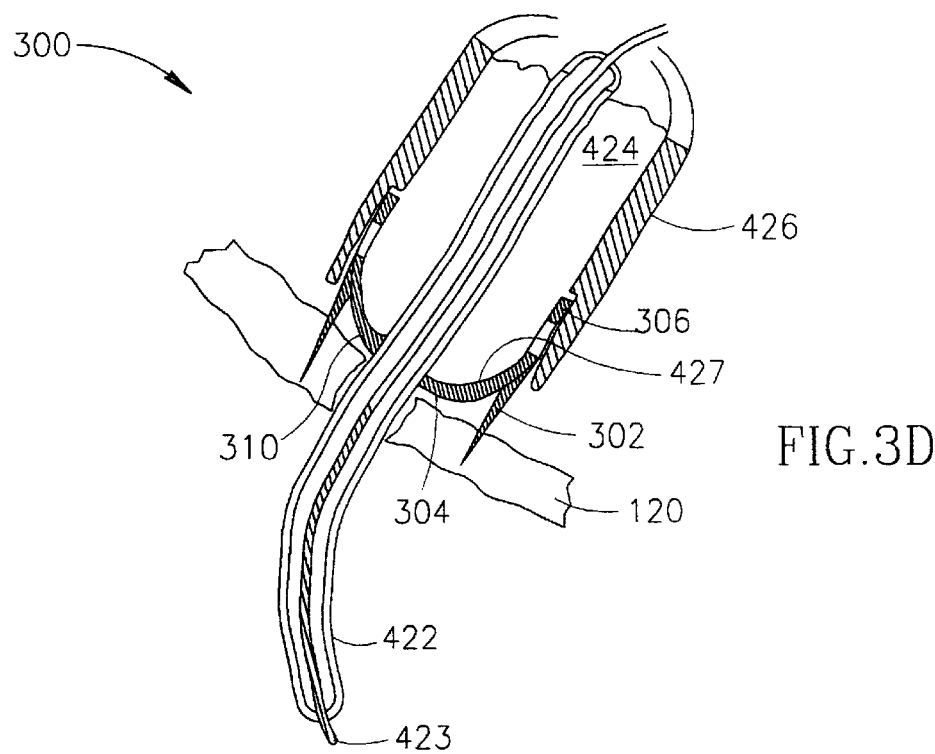
FIGS. 3D–3E illustrate a deployment of one of the devices of FIGS. 3A and 3B, in accordance with a preferred embodiment of the invention.
Figure 3E:
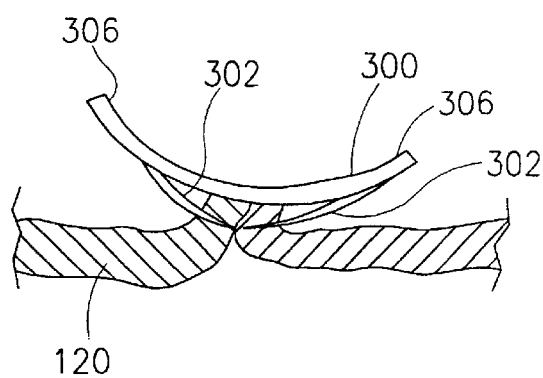

FIGS. 3D–3E illustrate a deployment of one of devices 300, 320 or 330, in accordance with a preferred embodiment of the invention. For description purposes, device 300 is assumed, however, all the devices may be similarly deployed. As in FIGS. 1B and 2B, a catheter 422 is inserted through ring 304 (catheter shown here with a guide wire 423). Tabs 306 are held in place between a tab holding tube 426 and a contra-element tube 424. The bending of bending element 310 is preferably supported by a curved portion 427 of contra-element tube 424. In this configuration, spikes 302 are pointed straight ahead and can easily engage vessel 120.

In FIG. 3E, which shows a cross-section of vessel 120, contra-element 426 is removed, releasing tabs 306. Base portions 303 (FIG. 3A) therefore urge the spike-engaged lips of vessel 120 against each other. It is noted that in device 300 of FIG. 3A, these events (releasing and radial contraction) will occur even if catheter 422 is not removed. Once catheter 422 is removed, the lips of the hole in vessel 120 will be pressed against each other and prevent leakage. This mechanism may not be suitable for all blood vessels, for example being suitable for veins and the femoral artery, but not for the aorta in situations when a radial hole closure is desired.

It should be noted that whether or not the lips of vessel 120 are everted by device 300 can be controlled, for example, by extending spikes 302(e.g., spacing apart base portions 303), eversion can be avoided.

It should also be noted that spikes 302 can be designed to penetrate vessel 102 to greater than the vessel wall thickness. Possibly, the spikes are made jagged at their edges, to allow them to engage both lips of the blood vessel, when deployed.

In device 300, the energy required to distort device 300 to seal the hole in vessel 120 is stored in bending element 310 and, possibly to some extent in ring 304. In contrast, in device 320, the energy is stored in ring 321.

Figure 3F:
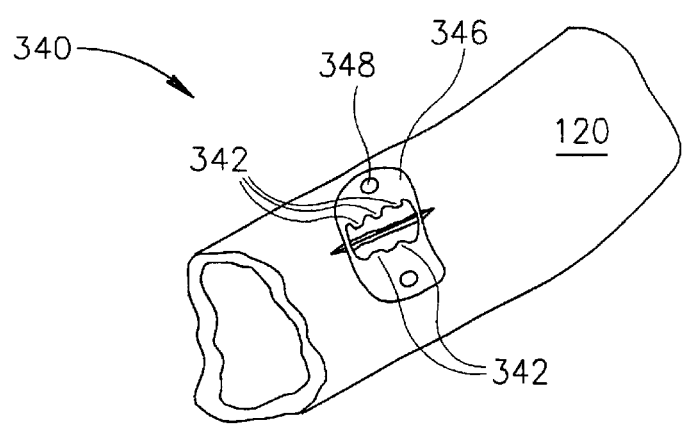
FIG. 3F illustrates an alternative, deployed, hole closure device in accordance with a preferred embodiment of the invention.

FIG. 3F illustrates an alternative hole closing device 340, similar to device 330, as deployed on vessel 120. Device 340 comprises a pair of tabs 346, possibly including holes 348 and a plurality of spikes 342 (only their base is shown). Unlike device 330 of FIG. 3C, and similar to devices 300 and 320, the spikes do not exactly face each others in pairs, allowing the spikes to be longer than half the distance between the spike bases. This also allows the spike bases to be close together, to promote eversion.

Figure 4A:
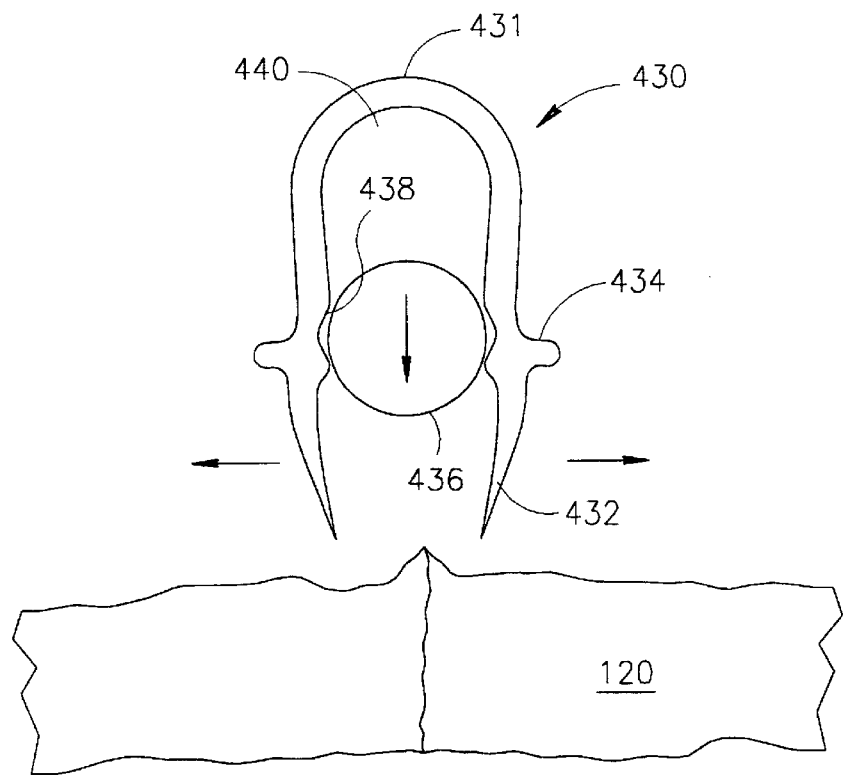
FIGS. 4A and 4B illustrate a blood vessel clip, in accordance with a preferred embodiment of the invention.
Figure 4B:
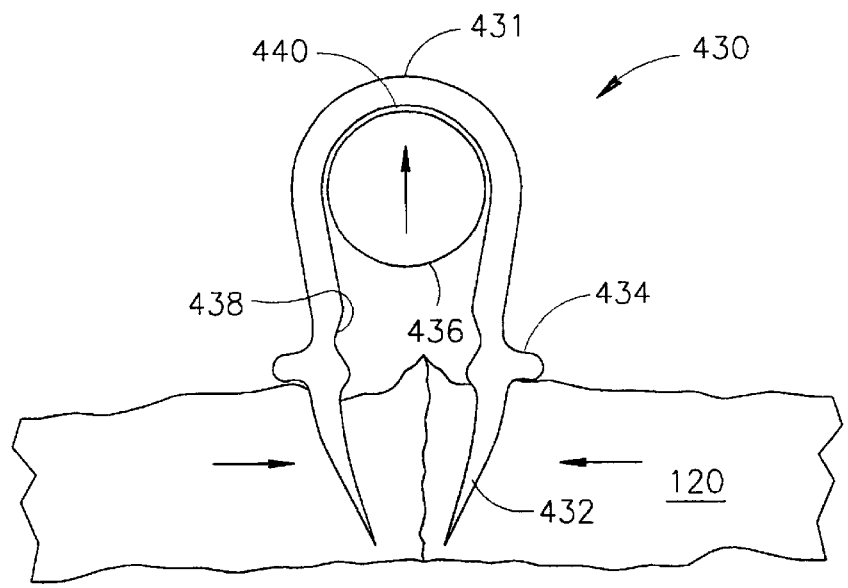

FIGS. 4A and 4B illustrate a blood vessel clip 430, in accordance with a preferred embodiment of the invention. Clip 430 comprises a pair of spikes 432 coupled together by a body 431. A pair of tabs 434 is provided. Preferably, tabs 434 act as tissue stops to prevent over insertion of spikes 432 in vessel 120. Alternatively or additionally, tabs 434 act as anchor points which can be used to hold clip 430 and/or advance it.

In FIG. 4A, a spacer element 436 is provided inside clip 430. Preferably, a contour 438 is provided in clip 430 to hold spacer element 436, however this is not essential. Clip 430 is then advanced into vessel 120, with one spike on either side of the opening in the vessel. Elastic energy for closing of the clip is preferably stored in body 431.

In FIG. 4B, spacer element 436 is retracted to a more spacious part 440 of body 431, allowing the spikes to move towards each other and close the hole in the blood vessel. After a short time, the clip may be removed. Alternatively, it is left in the body.

Alternatively to spacious part 440 being in the same plane as spikes 432, part 440 may be at an angle, or even perpendicular to the plane of spikes 432. Alternatively, no body part 440 is provided. Instead the spring action of body part 440 is provided by a flat spring. Although only two spike 432 are shown, a larger number, such as three or four may be provided, spaced apart along a line perpendicular to the figure plane. Alternatively to a body 431, these spikes may be mounted on a pivot bar.

Spacer element 436 is preferably removed by moving it perpendicular to the spike. Preferably spacer element 436 is a perpendicular protrusion on an elongate delivery tool.

Figure 5A:
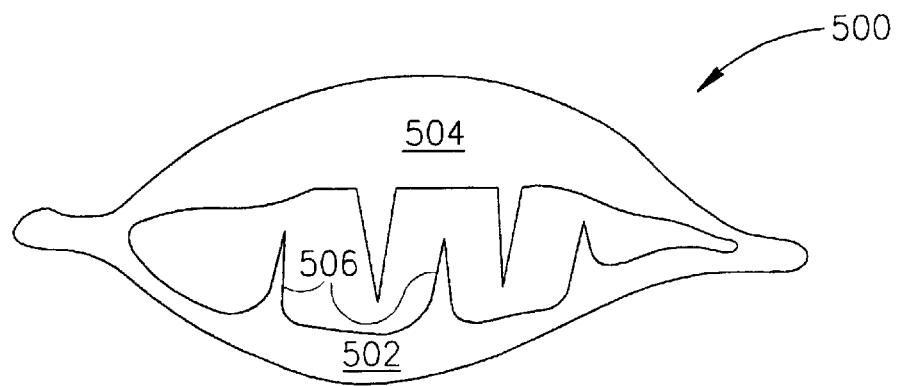
FIGS. 5A and 5B illustrate a bi-stable hole closure device, in accordance with a preferred embodiment of the invention.
Figure 5B:
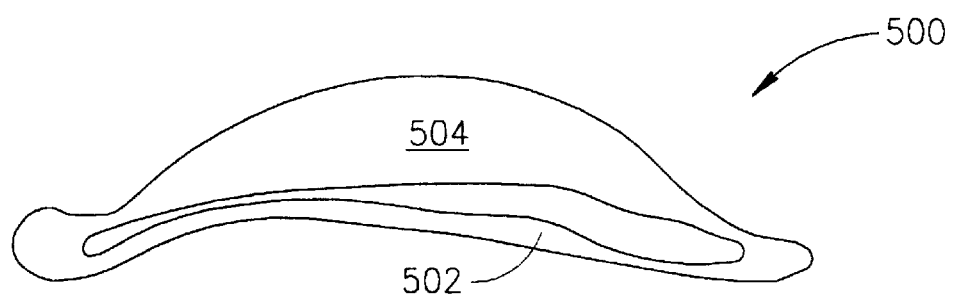

FIGS. 5A and 5B illustrate a bi-stable hole closure device 500, in accordance with a preferred embodiment of the invention.

FIG. 5A shows device 500 in an open configuration, a thick arm 540 and a thin arm 502 defining a lumen, into which project a plurality of spikes 506. In FIG. 5B, thin arm 502 is distorted to be concave, rather than convex, so that it substantially conforms to the curve of arm 504, rather than mirroring it. Spikes 506 are embedded in a vessel 120, so they are not shown. Various bi-stable mechanisms, which may be suitable, are described in PCT publication WO98/32412, the disclosure of which is incorporated herein by reference.

The above devices are preferably formed of stainless steel or a titanium alloy and use elastic, super elastic and/or shape-memory properties to distort when cannula 122 or other constraint is removed. Alternatively, the devices may be formed of a plastic material, especially a bio-absorbable material. Alternatively or additionally, the devices utilize a plastic deformation, for example deformation by an externally applied force.

The above devices can be adapted to a wide variety of blood vessels and/or other hollow body lumens, such as ducts, intestines, esophagus and trachea. It is noted however, that the devices of FIGS. 1 and 2 are better suited for an aorta, while the devices of FIGS. 3 and 5 are better suited for a femoral artery. The device of FIG. 4 is better suited for veins, where the pressure is lower. In a preferred embodiment of the invention, the hole closure devices are provided mounted on standard cannulas and catheters.

It will be appreciated that the above described methods of applying a vascular port and sealing a hole may be varied in many ways, including, changing the order of steps and the methods of distortion used. In addition, a multiplicity of various features, both of method and of devices have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. Also within the scope of the invention are surgical kits which include sets of medical devices suitable for making a single or a small number of ports or sealing holes of various sizes. When used in the following claims, the terms "comprises", "includes", "have" and their conjugates mean "including but not limited to".

It will be appreciated by a person skilled in the art that the present invention is not limited by what has thus far been described. Rather, the scope of the present invention is limited only by the following claims.

What is claimed is:

1. A blood vessel hole closure device, comprising:
   at least two blood vessel engaging structures, each comprising a base;

at least one second, deformable, structure, coupled to said at least two blood-vessel engaging structures and having a first deformation state and a second deformation state, wherein said at least one second deformable structure urges said two blood vessel engaging structures towards each other when going from said first deformation state to said second deformation state, wherein, said change in deformation state is at least partially mechanically decoupled from each of said blood-vessel engaging structures, such that it does not effect a substantial deformation of said blood-vessel engaging structure relative to said base.

2. A device according to claim 1, wherein said at least one second deformable structure comprises a deformable ring-like structure, adapted to enclose a blood vessel cannula-like tube in said first deformation state.

3. A device according to claim 2, comprising a ring-like element on which said at least one deformable structure is mounted and, wherein said at least one second deformable structure comprises at least two bending elements that couple said blood-vessel engaging structures to said ring-like element.

4. A device according to claim 3, wherein said ring-like element defines a lumen that has a substantially same radius in said deformation states.

5. A device according to claim 1, wherein said blood vessel engaging structures each comprise at least one spike adapted for insertion into a wall of a blood vessel.

6. A device according to claim 1, wherein said blood vessel engaging structures each comprise at least two spikes adapted for insertion into a wall of a blood vessel.

7. A device according to claim 5, wherein said blood vessel engaging structures each comprise a pivot bar on which said spike is mounted.

8. A device according to claim 7, wherein said blood vessel engaging structures each comprise at least one tab, mounted on said pivot bar.

9. A device according to claim 8, wherein said tab comprises an anchor for holding said tab.

10. A device according to claim 7, wherein said pivot bar comprises a hinge at either end.

11. A device according to claim 7, wherein said pivot bar is straight.

12. A device according to claim 7, wherein said pivot bar is mounted on a spacer that spaces said pivot bar from said at least one second deformable structure.

13. A device according to claim 1 wherein said base is adapted for abutment against the blood vessel.

14. A device according to claim 13, wherein said bases are spaced apart a distance sufficient to prevent eversion of a blood vessel in which a hole is closed.

15. A device according to claim 13, wherein said bases are spaced apart a distance sufficient to cause at least partial eversion of a blood vessel in which a hole is closed.

16. A device according to claim 1 wherein said at least one second deformable structure comprises at least two deformable structures connected by at least one joint.

17. A device according to claim 16, wherein said joint is elastic.

18. A device according to claim 16, wherein said joint comprises a segment of a circle.

19. A device according to claim 16, wherein said joint is free turning for at least a range of angles.

20. A device according to claim 16, wherein said joint is integral with said at least two deformable structures.

21. A device according to claim 16, wherein said joint is formed by an interlocking of the two deformable structures.

22. A device according to claim 1, wherein said at least one deformable structure comprises a bar.

23. A device according to claim 1, wherein at least one of said blood vessel engaging structures is radially external to said at least one deformable structure.

24. A device according to claim 1, wherein at least one of said blood vessel engaging structures is radially internal to said at least one deformable structure.

25. A hole closure device, comprising:

at least one pivot bar;

at least one spike mounted on said bar such that rotating said spike around said bar twists said pivot bar; and a base to which said at least one bar is coupled and which base does not encompass said bar.

26. A device according to claim 25, comprising at least one structure which supports said pivot bar and which couples said pivot bar to said base.

27. A device according to claim 25, wherein said base comprises a deformable ring-like element.

28. A device according to claim 27, wherein said base comprises at least two hinges at opposite ends of said base.

29. A hole closure device, comprising:

a deformable ring-like structure;

a plurality of spikes coupled to said structure, each of said spike comprising a base; and a coupling structure coupling said base to said ring-like structure, wherein said base is radially spaced from said ring-like structure by said coupling structure, at least the length of said spike.

30. A device according to claim 29, wherein said spikes are each mounted on a pivot bar.

31. A hole closure device comprising:

a first body part comprising:

a plurality of blood-vessel engaging structures, adapted to remain outside a blood vessel; and at least a first hinge part coupled to said plurality of blood vessel engaging structures; and a second body part comprising:

a plurality of blood-vessel engaging structures adapted to remain outside a blood vessel; and at least a second hinge part coupled to said plurality of blood vessel engaging structures, wherein said first and said second hinge parts are adapted to interlock to form a hinge.

32. A blood vessel clip, comprising:

at least two spikes;

at least one tab, perpendicular to at least one of said spikes; and an elastic body connecting the two spikes, said body having a greater inner dimension away from said spike than nearer said spike.

33. A bi-stable hole closure device, comprising:

at least two arms, coupled to each other at either end thereof, wherein:

a first one of said arms is less flexible than a second one of said arms, and wherein said second arm is adapted to have two stable states, one state in which the second arm is spaced from said first arm and one state in which said second arm is adjacent said first arm; and a plurality of blood-vessel engaging elements mounted on each of said arms.

* * * * *

UNITED STATES PATENT AND TRADEMARK OFFICE
CERTIFICATE OF CORRECTION

PATENT NO. : 6,726,704 B1
DATED : April 27, 2004
INVENTOR(S) : Amir Loshakove et al.

It is certified that error appears in the above-identified patent and that said Letters Patent is hereby corrected as shown below:

Title page,
Item [63], Related U.S. Application Data, before "Continuation-in-part of application No. 09/701,531" add -- Continuation-in-part of application No. 09/936,789, filed as application No. PCT/IL99/00674 on December 9, 1999, and a continuation-in-part of application No. 09/936,806, filed as application No. PCT/IL99/00670 on December 8, 1999 and --

Signed and Sealed this

Tenth Day of August, 2004

JON W. DUDAS
*Acting Director of the United States Patent and Trademark Office*